(12) United States Patent  
Likhotvorik et al.

(10) Patent No.: US 7,348,430 B2
(45) Date of Patent: Mar. 25, 2008

(54) PRODUCTION OF OPIOID ANALGESICS

(75) Inventors: Igor R. Likhotvorik, Culver, IN (US); Joseph J. Lisowski, Knox, IN (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 480 days.

(21) Appl. No.: 11/040,235

(22) Filed: Jan. 21, 2005

(65) Prior Publication Data

US 2006/0167258 A1    Jul. 27, 2006

(51) Int. Cl.
*C07D 489/02*    (2006.01)
(52) U.S. Cl. .......................... 546/44; 546/45
(58) Field of Classification Search ................ 546/44, 546/45
See application file for complete search history.

(56) References Cited

U.S. PATENT DOCUMENTS

| | | | |
|---|---|---|---|
| 1,731,152 A | 10/1929 | Schopf | |
| 2,544,291 A | 3/1951 | Baizer | |
| 2,628,962 A | 2/1953 | Homeyer et al. | |
| 2,649,454 A | * 8/1953 | Rapoport | 546/45 |
| 2,654,756 A | 10/1953 | Homeyer et al. | |
| 2,715,626 A | 8/1955 | Pfister et al. | |
| 5,571,685 A | 11/1996 | Hailes et al. | |
| 5,847,142 A | 12/1998 | Mudryk et al. | |

FOREIGN PATENT DOCUMENTS

| | | |
|---|---|---|
| DE | 441613 | 3/1927 |
| GB | 285404 | 5/1929 |
| WO | WO 0134608 | 5/2001 |

OTHER PUBLICATIONS

J. Am. Chem. Soc (1936), 58, 1457.
Helv. Chim. Acta. (1968), 51,381.
J. Org. Chem. (1956), 21,370.
J. Med. Chem. (1976), 19, 1171.
J. Org. Chem. (1938), 3, 204.
Arch. Pharm ( 1920), 258,295.
Synth. Commun. (2000), 30, 3195.

* cited by examiner

*Primary Examiner*—Bernard Dentz
(74) *Attorney, Agent, or Firm*—Morgan Lewis & Bockius LLP

(57) ABSTRACT

The present invention includes a process for the manufacture of dihydrothebaine, dihydrocodeinone enol acetate, hydrocodone, and analogs thereof by reacting dihydrocodeine or analogs thereof with benzophenone in the presence of potassium tert-alkylate in a hydrocarbon solvent to generate a reaction mixture containing an enolate of the corresponding ketone, followed by addition of the reaction mixture to the electrophilic agent and isolation of the product.

17 Claims, No Drawings

PRODUCTION OF OPIOID ANALGESICS

BACKGROUND OF THE INVENTION

Hydrocodone and dihydrocodeinone enol acetate are semisynthetic narcotic analgesics useful in the treatment of acute or chronic pain. Hydrocodone, dihydrocodeinone enol acetate and dihydrothebaine are important intermediates for the synthesis of other opioid narcotic analgesics, including oxycodone, dihydrocodeine, and metopon.

A variety of different chemically non-related approaches have been used for the preparation dihydrothebaine, dihydrocodeinone enol acetate, hydrocodone, and analogs thereof.

For example, dihydrothebaine was synthesized by partial reduction of thebaine (UK Pat. No. 285404; J. Am Chem. Soc (1936), 58, 1457; Helv. Chim. Acta. (1968), 51, 381) or through hydrocodone methylation processes (J. Org. Chem. (1956), 21, 370; J. Med. Chem. (1976), 19, 1171).

Further, acetylation of hydrocodone with acetic anhydride affords dihydrocodeinone enol acetate (J. Org. Chem. (1939), 3, 204; U.S. Pat. No. 1,731,152).

Hydrocodone can be prepared by reduction of codeinone (Arch. Pharm (1920), 258, 295; U.S. Pat. No. 5,571,685) or thebaine (DE Pat. No. 441,613), through isomerization of codeine in the presence of noble metal catalysts (examples may be found in "The Chemistry of the Morphine Alkaloids" by Bentley, K. W.; U.S. Pat. No. 2,544,291; U.S. Pat. No. 5,847,142, WO Pat. No. 0134608) or by Oppenauer oxidation of dihydrocodeine in the presence of aluminum alkoxides (U.S. Pat. No. 2,628,962; U.S. Pat. No. 2,654,756, U.S. Pat. No. 2,715,626).

Oppenauer oxidation of dihydrocodeine can be accomplished more conveniently in the presence of potassium tert-butoxide (U.S. Pat. No. 2,649,454; Synth. Commun. (2000), 30, 3195). Although this type of oxidation may be the method of choice for modern manufacturing, the quality of the resulting hydrocodone is unreliable due to the uncontrollable build up of process by-products, especially hydrocodone aldol dimers. Product purification, especially separation of the desired product from the dimer by-product that has properties very similar to the desired ketone product, is currently very difficult and adds multiple purification steps to the process, resulting in substantial yield loss.

SUMMARY OF THE INVENTION

The present invention provides a general method for the preparation of 4,5-epoxymorphinan compounds of formula (I)

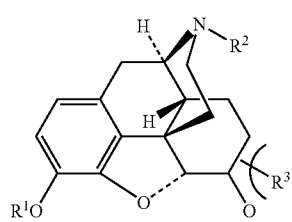

wherein $R^1$ is an alkyl group, a substituted alkyl group, methyl, substituted methyl or alcohol protecting group;

$R^2$ is hydrogen, an alkyl group, a substituted alkyl group, methyl, substituted methyl or amine protecting group, $R^3$ is hydrogen, an alkyl group, a substituted alkyl group, methyl, substituted methyl or alcohol protecting group.

In one embodiment, compounds of formula (I) can be represented by the formulae (IA) and (IB) as hereinafter detailed:

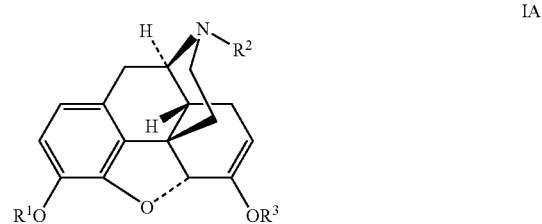

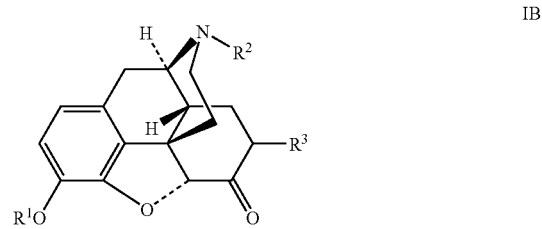

A method for preparing compounds of formula I according to the present invention includes the steps of
(i) reacting an alcohol of formula (II)

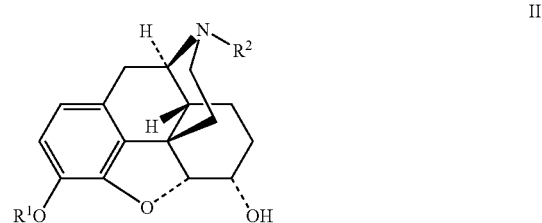

wherein $R^1$ and $R^2$ are as hereinbefore defined, with a ketone, typically a aromatic ketone. In one embodiment, benzophenone, 9-fluorenone, anthrone, dibenzosuberone, anthraquinone, and/or 2,2-dimethylpropiophenone, can be used with and a potassium tert-alkylate in hydrocarbon solvent to generate a reaction mixture containing enolate of formula (III)

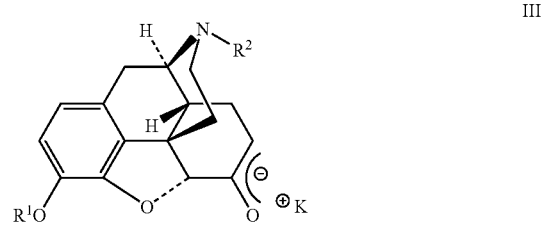

wherein $R^1$ and $R^2$ are as hereinbefore defined; and then performing one of the following alternative steps (ii).

Alternative Step ii(A)

In one embodiment, alternative step ii(A) includes the step of adding reaction mixture containing an enolate of formula (III) to an electrophilic agent of formula (IV)

$$R^3X \qquad \text{IV}$$

wherein $R^3$ is as hereinbefore defined and X is a leaving group to yield a compound of formula (I), or Alternative Step ii(B)

Alternative step ii(B) includes the step of adding an electrophilic agent of formula (IV)

$$R^3X \qquad \text{IV}$$

wherein $R^3$ is as hereinbefore defined, except it is not typically hydrogen, and X is a leaving group, to the reaction mixture containing an enolate of formula (III) to yield a compound of formula (I).

Step (iii) includes the step of isolating a compound of formula (I).

DETAILED DESCRIPTION OF THE INVENTION

The present invention provides a general method for the production of dihydrocodeinone enol acetate, dihydrothebaine, hydrocodone, and analogs thereof. In one embodiment, the present invention further provides processes which allow for the efficient, economical, and practical preparation of desired compounds. In one embodiment, the present invention also provides processes for the manufacture of desired compounds in an environmentally-friendly way.

The process of the present invention is based on the discovery that the intermediate ketone, formed during Oppenauer oxidation of the parent alcohol of formula (II) with benzophenone in the presence of potassium tert-alkylate in hydrocarbon solvent does not reside in the reaction mixture in any detectable amount, but surprisingly undergoes instantaneous, conversion, to the corresponding enolate of formula (III), as shown in the following reaction scheme (Scheme 1). In one embodiment, the conversion is about 90.0% to about 100%, more typically about 99.9% to about 100%, wherein "about" means + or −10% of the value indicated and is inclusive of the value indicated.

Scheme 1

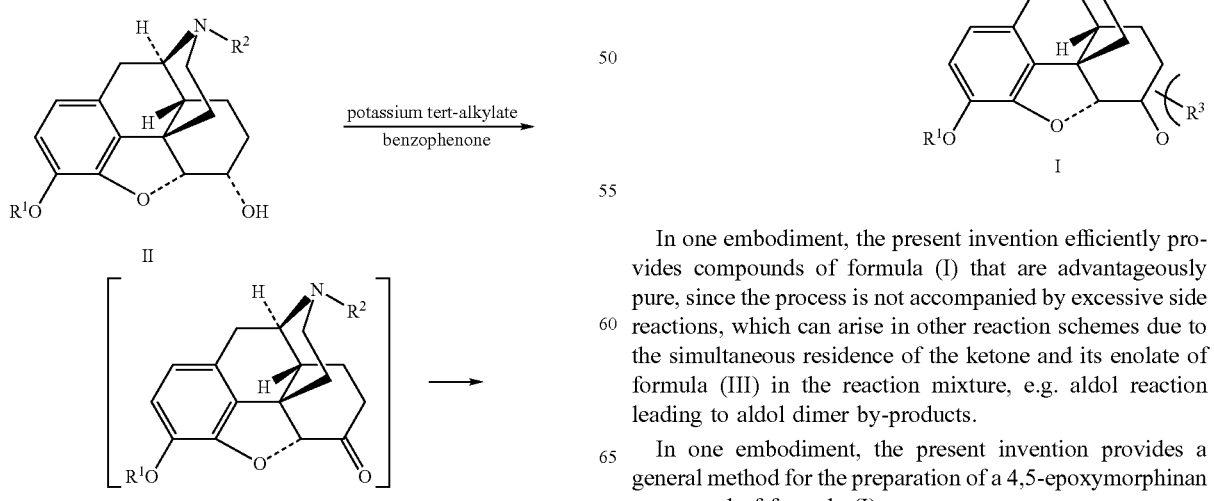

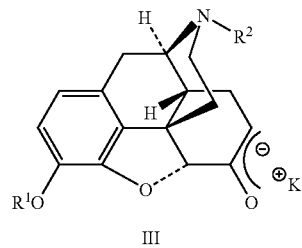

Because completeness of the intermediate ketone conversion to the enolate of formula (III) is thus spontaneously achieved, in one embodiment quenching the reaction mixture with an electrophilic agent of formula (IV) affords highly specific products as set forth in the following reaction scheme (Scheme 2).

Scheme 2

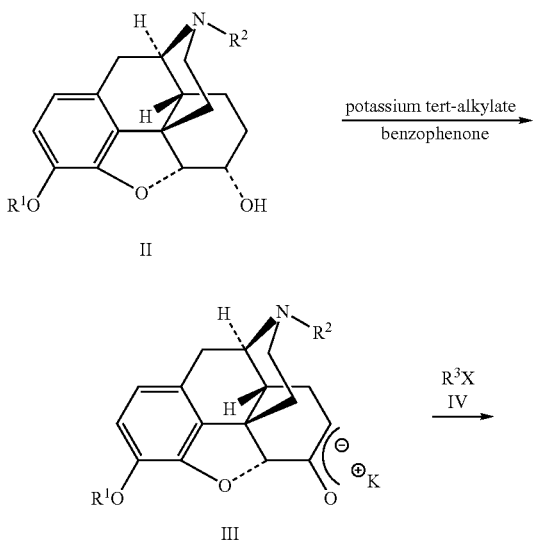

In one embodiment, the present invention efficiently provides compounds of formula (I) that are advantageously pure, since the process is not accompanied by excessive side reactions, which can arise in other reaction schemes due to the simultaneous residence of the ketone and its enolate of formula (III) in the reaction mixture, e.g. aldol reaction leading to aldol dimer by-products.

In one embodiment, the present invention provides a general method for the preparation of a 4,5-epoxymorphinan compound of formula (I)

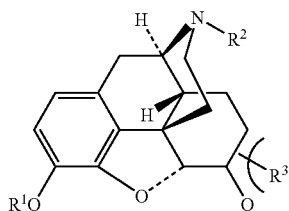

wherein

R$^1$ is a lower alkyl or substituted lower alkyl, methyl, substituted methyl or alcohol protecting group;

R$^2$ is hydrogen, a lower alkyl or substituted lower alkyl, methyl, substituted methyl or amine protecting group, R$^3$ is hydrogen, a lower alkyl or substituted lower alkyl, methyl, substituted methyl or alcohol protecting group.

In one embodiment, the method includes the following steps.

Step i—Reaction Involving the Alcohol

Step i includes the step of reacting an alcohol of formula (II)

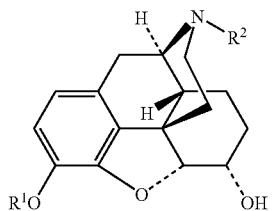

wherein R$^1$ and R$^2$ are as hereinbefore defined, with a ketone and a metal alkoxide in hydrocarbon solvent to generate a reaction mixture containing an enolate of formula (III). In one embodiment an aromatic ketone such as benzophenone can be used and a metal alkoxide such as potassium tert-alkylate can be used. In other embodiments, one or more of 9-fluorenone, anthrone, dibenzosuberone, anthraquinone, 2,2-dimethylpropiophenone can be used. In certain embodiments, the metal alkoxide should be: a) sufficiently reactive to activate the Oppenauer oxidation; b) strongly basic—preferably just enough to allow transformation of the intermediate ketone to the enolate, but not overly basic, since it may induce by-products formation; c) relatively soluble in the reaction mixture; and/or d) non-oxidizable during the Oppenauer reaction. In certain embodiments, a suitable class of compounds for this invention includes alkali metal tert-alkoxides (commonly referred to as alkali metal tert-alkylates) and metal or salt (e.g., potassium) tert-alkoxides (or tert-alkylates). In the above, benzophenone can be obtained from several manufacturers or distributors including Sigma-Aldrich Chemical Co., catalog # B930-0. Potassium t-butoxide powder and potassium t-amylate solution in cyclohexane can be purchased from Callery Chemical Co. Dihydrocodeine can be synthesized by hydrogenation of codeine phosphate, purchased from Mallinckrodt Inc.

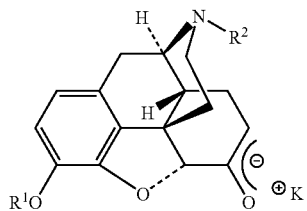

wherein R$^1$ and R$^2$ are as hereinbefore defined.

In one embodiment of the process, an alcohol of formula (II) can be dihydrocodeine, wherein R$^1$ and R$^2$ are both methyl. In one embodiment, the alcohol is reacted with a ketone, e.g., benzophenone, and potassium tert-alkylate in hydrocarbon solvent to generate a reaction mixture containing an enolate of formula (III), which is the enolate of hydrocodone.

With respect to step i, suitable hydrocarbon solvents for use herein include cyclohexane, toluene, xylene and xylene-like compoundsd, and heptane, and combinations thereof.

In one embodiment, the molar ratio of compound of formula (II) to benzophenone can be in the range of about 1:3 to about 1:20, preferably of about 1:6 to about 1:9.

In one embodiment, suitable potassium tert-alkylates for use herein may be selected from the group consisting of potassium tert-amylate and potassium tert-butoxide, and combinations thereof.

In one embodiment, potassium tert-alkylate may be present in the reaction mixture in amounts between about 1 to about 5 equivalents relative to the amount of compound of formula (II), preferably between about 1.4 to about 4 equivalents.

In one embodiment, reaction with potassium tert-alkylate is suitably carried at temperatures in the range of about 5° C. to about 110° C., preferably of about 15° C. to about 80° C., and most preferably of about 20° C. to about 50° C.

Step ii—Combining an Enolate With and Electrophilic Agent

After the completion of step i, one of the following two alternative steps, ii(A) or ii(B), can be performed on the reaction mixture.

Alternative Step ii(A)

Alternative Step ii(A) includes the step of adding a reaction mixture containing an enolate of formula (III) to an electrophilic agent of formula (IV)

R$^3$X    IV wherein R$^3$ is as hereinbefore defined and X is leaving group (i.e., a portion of a molecule that is discharged from the molecule upon reaction), to yield a compound of formula (I).

In one embodiment, compounds of formula (I) can be represented by the formulae (IA) and (IB) as hereinafter detailed:

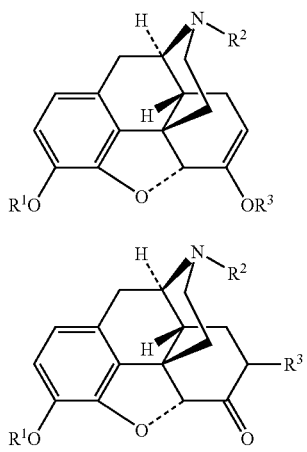

IA

IB wherein R¹, R², and R³ are as hereinbefore defined.

Alternative Step ii(B)

Alternative Step ii(B) includes the step of adding an electrophilic agent of formula (IV)

R³X          IV wherein R³ is as hereinbefore defined, except hydrogen, and X is leaving group, to the reaction mixture containing an enolate of formula (III), to yield a compound of formula (I).

With respect to steps ii(A) and ii(B), in one embodiment, leaving groups useful in the present invention include, but are not limited to, a halide (e.g. chloride, bromide, iodide), a sulfonate (e.g. tosylate, mesylate, triflate), a sulfate (e.g. alkyl sulfate), a phosphate (e.g. alkyl phosphate, aryl phosphate), a carboxylate (e.g. acetate, propionate), an alkoxyl (e.g. methylate, t-butylate), and a hydroxyl. Other suitable leaving groups are known in the art.

Further, in one embodiment because the reaction with an electrophilic agent of formula (IV) in step ii may involve both an enolate of formula (III) and a potassium tert-alkylate, due to the chemical nature of these species, the electrophilic agent of formula (IV) is used in amount of at least one equivalent relative to the amount of potassium tert-alkylate.

An embodiment of the present invention provides a method for the production of 4,5-epoxymorphinan compounds of formula (IA) as illustrated by Scheme 3.

Scheme 3

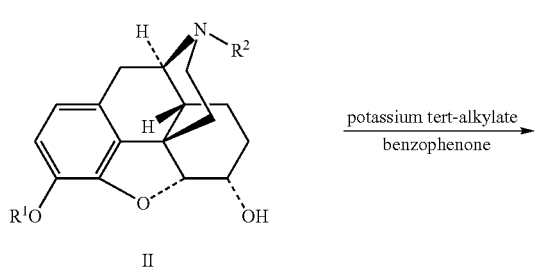

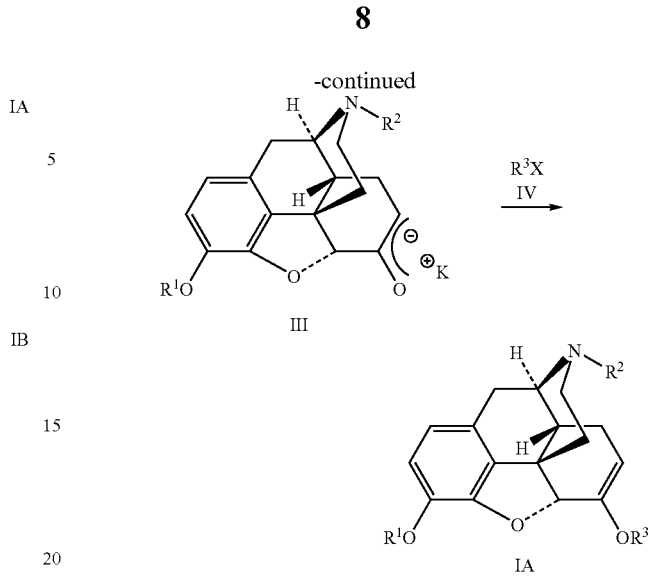

Another aspect of the present invention provides a process for the production of 4,5-epoxymorphinan compounds of formula (IB) as illustrated by Scheme 4.

Scheme 4

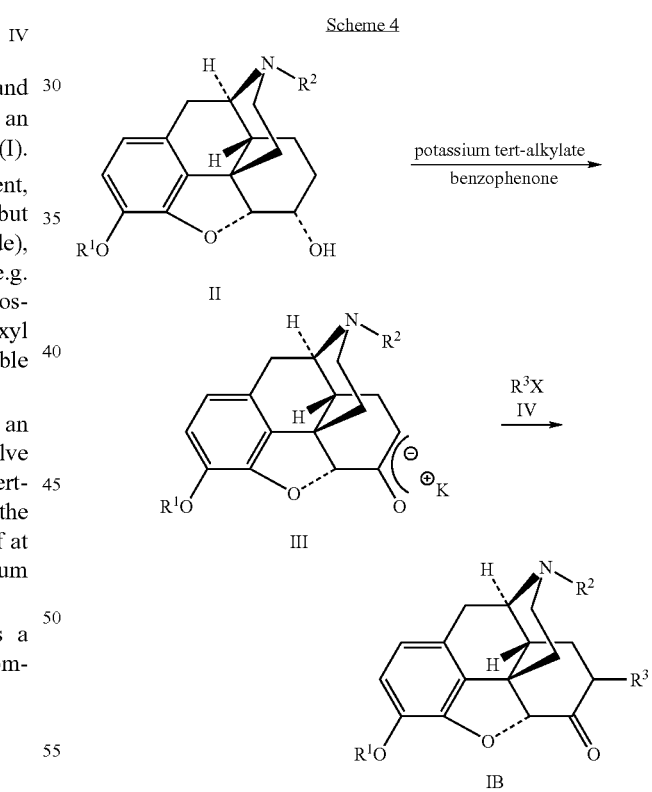

In an embodiment of step ii, a reaction mixture containing an enolate of hydrocodone from step i can be added to the electrophilic agent of formula (IV).

In one embodiment, the electrophilic agent can be dimethyl sulfate, wherein R³ is methyl and X is methyl sulfate, or alternatively by adding dimethyl sulfate to the reaction mixture containing an enolate of hydrocodone to yield a compound of formula (IA), which is dihydrothebaine, wherein R¹, R², and R³ are methyl groups.

In another embodiment of step ii, the reaction mixture containing an enolate of hydrocodone can be added to the electrophilic agent of formula (IV), wherein the electrophilic agent can be acetic anhydride, wherein $R^3$ is acetyl and X is acetate, or alternatively by adding acetic anhydride to the reaction mixture containing an enolate of hydrocodone to yield a compound of formula (IA), which is dihydrocodeinone enol acetate, wherein $R^1$ and $R^2$ are both methyl, and $R^3$ is acetyl.

In another embodiment of step ii, adding a reaction mixture containing an enolate of hydrocodone to the electrophilic agent of formula (IV), which can be water, wherein $R^3$ is hydrogen and X is hydroxyl, alcohol, wherein $R^3$ is alkyl and X is hydroxyl, or an acid, wherein $R^3$ is hydrogen and X is a leaving group corresponding to the anion of the acid, or a mixture of water and the acid, yields a compound of formula (IB), which is hydrocodone, and wherein $R^1$ and $R^2$ are both methyl, and $R^3$ is hydrogen.

It will be understood that the alternative addition of the electrophilic agent of formula (IV), wherein the electrophilic agent is water, wherein $R^3$ is hydrogen and X is hydroxyl, or an acid, wherein $R^3$ is hydrogen and X is a leaving group corresponding to the anion of the acid, or a mixture of water and the acid, to the reaction mixture containing an enolate of hydrocodone, can lead to conditions which favor generating an undesirable process by-product hydrocodone aldol dimer along with desired hydrocodone, as illustrated by Example 3.

It will also be understood that various modifications with respect to reaction conditions, starting materials, substituents and the nature of the electrophilic agent of formula (IV) may be performed by those skilled in the art to direct the process of the present invention towards preferred production of compounds of formula (IA) or compounds of formula (IB), as described herein and in Examples 1, 2 and 3.

Step iii—Isolation of the Compound

After performing either alternative step ii(A) or ii(B), step iii includes the step of isolating compound of formula (I). In one embodiment, a precipitation reaction can be used to isolate the compound. In one embodiment, the compound can be isolated by using a base to cause precipitation.

In one embodiment, a method of the present invention yields hydrocodone of desirable yield and high purity, substantially free from hydrocodone aldol dimer, thus providing an improved process for manufacturing of hydrocodone from dihydrocodeine.

Industrial Scale Up

The process in accordance with the present invention can be performed on the industrial scale by adding the alcohol of formula (II), a ketone (e.g., benzophenone), and potassium tert-alkylate to the hydrocarbon solvent, agitating the mixture at suitable temperature until the reaction is completed as determined by a suitable analytical technique (e.g. TLC, HPLC), then quenching the mixture containing the enolate of formula (III) by adding it to the electrophilic agent of formula (IV), or alternatively, by adding the electrophilic agent of formula (IV), where applicable, to the mixture containing the enolate of formula (III), with agitation, to yield said 4,5-epoxymorphinan compound of formula (I), which can be isolated from the reaction mixture using techniques that are well known to those skilled in the art, as described elsewhere herein.

In one embodiment, the process of the present invention has the advantage that various 4,5-epoxymorphinan compounds of formula (I) may be prepared using one general processing stream, and this may be achieved in fewer steps and less time than in processes described in the prior art, without related losses of yield, thereby producing the products in desirable purity. Furthermore, the process of the invention has the advantage that 4,5-epoxymorphinan compounds of formula (I) may be obtained more conveniently, at lower cost, and by using environmentally more friendly chemicals, than when obtained through the processes described in the prior art.

The following examples are presented to further illustrate the invention but are not meant to be limiting in any way.

EXAMPLE 1

Dihydrothebaine

Dihydrocodeine (0.504 g) and benzophenone (2.22 g) were dissolved in cyclohexane (9 mL), then potassium tert-butoxide (0.59 g) was added, and the mixture was agitated under nitrogen at 30-50° C. for 4 hours and cooled to room temperature. Dimethyl sulfate (0.5 mL) was added dropwise to reaction mixture over a period of 20 minutes with cooling to 20° C. and efficient stirring. The mixture was agitated for 18 hours at room temperature, then extracted with 1.5N acetic acid (2.5 mL) and water (0.5 mL). The combined aqueous extracts (4.48 g) contained 0.426 g dihydrothebaine according to an HPLC assay. Purified dihydrothebaine, prepared by the Homeyer method (*J. Org. Chem.* (1956), 21, 370), was used as a reference standard for the HPLC assay. Solid dihydrothebaine was obtained from the solution via precipitation with aqueous sodium hydroxide.

EXAMPLE 2

Dihydrocodeinone Enol Acetate

Dihydrocodeine (0.502 g) and benzophenone (2.24 g) were dissolved in cyclohexane (9 mL), then potassium tert-butoxide (0.59 g) was added, and the mixture was agitated under nitrogen at 30-40° C. for 4 hours, then cooled to room temperature. Acetic anhydride (1 mL) was added to the reaction mixture in one portion with efficient stirring. The mixture was agitated for 30 minutes at room temperature and assayed by HPLC to contain 0.535 g of dihydrocodeinone enol acetate. Purified dihydrocodeinone enol acetate, prepared by the Small method (*J. Org. Chem. Soc* (1939), 3, 204), was used as a reference standard for the HPLC assay. Solid dihydrocodeinone enol acetate was obtained from the mixture via extraction with 1.5N acetic acid as in the previous example, followed by precipitation with aqueous ammonia.

EXAMPLE 3

Hydrocodone

Experiment A (reference): Hydrocodone preparation, including addition of acidified water to the reaction mixture containing hydrocodone enolate and potassium tert-butylate Dihydrocodeine (5 g) and benzophenone (30.05 g). were added, under nitrogen, to a mechanically agitated mixture of benzene (100 mL, Experiment A1, Table 1) or cyclohexane (100 mL, Experiment A2, Table 1) and potassium tert-butoxide (5.6 g). The mixture was agitated at reflux (80-82° C.) for 2.5 hours and cooled to room temperature. 3N hydrochloric acid (25 mL) was added to the mixture over a period of 0.5 hours with cooling to 6-16° C. The aqueous layer was separated, the organic layer was washed with water (10 mL), and the aqueous extracts were combined. The resulting solution was analyzed by HPLC to determine the hydrocodone content [H %] and also the content of the major impurity, hydrocodone aldol dimer [HAD %] (Table 1).

Experiment B: Hydrocodone preparation, including the addition of an oxidation mixture containing hydrocodone enolate and potassium tert-butylate to acidified water.

Dihydrocodeine (5 g) and benzophenone (21.8 g) were added under nitrogen to the stirred mixture of cyclohexane (90 mL) and potassium tert-butoxide (5.6 g). The mixture was agitated at 60° C. for 1.5 hours, cooled to room temperature, and transferred slowly to vigorously-agitated 1.5N aqueous acetic acid (53 mL) over a period of 16 minutes with cooling to 6-14° C. The aqueous layer was separated, the organic layer was washed with 1.5N acetic acid (10 mL), and the aqueous extracts were combined. The solution was analyzed by HPLC to determine the hydrocodone content [H %] and also to determine the content of the major impurity: hydrocodone aldol dimer [HAD %] (Table 1).

Experiment C: Hydrocodone preparation, including the addition of an oxidation mixture containing hydrocodone enolate and potassium tert-amylate to acidified water.

Potassium tert-amylate 15% solution in cyclohexane (102 mL) was added, under nitrogen, to a stirred solution of dihydrocodeine (10.4 g) and benzophenone (48.0 g) in cyclohexane (80 mL). The mixture was agitated at 25-32° C. for 5 hours, then transferred slowly to a vigorously-agitated 1.5N aqueous acetic acid solution (110 mL) over a period of 40 minutes with cooling to about 0° C. The aqueous layer was separated, the organic layer was washed with water (5 mL), and the aqueous extracts were combined. The solution was analyzed by HPLC to determine the hydrocodone content [H %] and also to determine the content of the major impurity: hydrocodone aldol dimer [HAD %] (Table 1).

TABLE 1

| Experiment | Method for hydrocodone enolate quenching | H % | HAD % |
| --- | --- | --- | --- |
| A1 | Acidified water is added to the reaction mixture | 90.1 | 7.4 |
| A2 | Acidified water is added to the reaction mixture | 88.4 | 8.6 |
| B | Reaction mixture is added to acidified water | 99.3 | 0.2 |
| C | Reaction mixture is added to acidified water | 97.0 | 0.7 |

The results in Table 1 indicate that if acidified water is added to the reaction mixture containing hydrocodone enolate (Experiment A), excessive side reactions occur, leading to the highest levels of the major by-product, hydrocodone aldol dimer [HAD]. The results in Table 1 also show that significant yield and desired purity of hydrocodone may be achieved when the reaction mixture containing hydrocodone enolate is slowly added to acidified water.

It will be appreciated by persons skilled in the art that numerous variations and/or modifications may be made to the invention shown in the specific embodiments without departing from the spirit and scope of the invention as broadly described. Further, each and every reference cited herein is hereby incorporated by reference in its entirety.

The invention claimed is:
1. A process for the preparation of a 4,5-epoxymorphinan compound of formula (I)

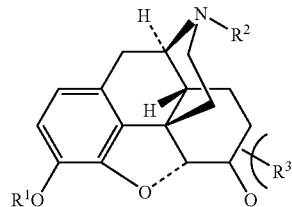

wherein
$R^1$ is methyl, substituted methyl or alcohol protecting group;
$R^2$ is hydrogen, methyl, substituted methyl or amine protecting group,
$R^3$ is methyl, substituted methyl or alcohol protecting group;
comprising the steps of
(i) reacting an alcohol of formula (II)

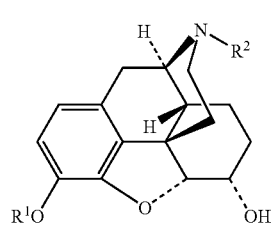

wherein $R^1$ and $R^2$ are as hereinbefore defined, with benzophenone and potassium tert-alkylate in hydrocarbon solvent to generate a reaction mixture containing the enolate of formula (III)

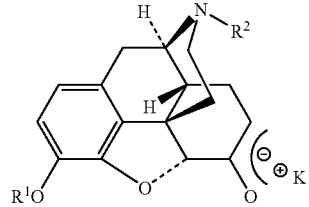

wherein $R^1$ and $R^2$ are as hereinbefore defined; and
(ii) adding reaction mixture containing the enolate of formula (III) to the electrophilic agent of formula (IV)

$$R^3X \qquad IV$$

wherein $R^3$ is as hereinbefore defined and X is a leaving group, to yield a compound of formula (I), and
(iii) isolating the compound of formula (I).
2. The process of claim 1, wherein the hydrocarbon solvent is selected from the group consisting of cyclohexane, toluene, heptane and combinations thereof.
3. The process of claim 1, wherein the potassium tert-alkylate is selected from the group consisting of potassium tert-amylate, potassium tert-butoxide, and combinations thereof.

4. The process of claim 1, wherein X is a leaving group selected from the group consisting of halide, sulfonate, sulfate, phosphate, phosphite, carboxylate, alkoxyl, and hydroxyl.

5. The process of claim 1, wherein said compound of formula (I) is a compound of formula IA

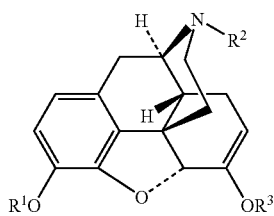

wherein $R^1$, $R^2$, and $R^3$ are as defined hereinbefore.

6. The process of claim 1, wherein the molar ratio of said alcohol of formula (II) to said benzophenone is in the range of about 1:3 to about 1:20.

7. The process of claim 6, wherein the molar ratio of said alcohol of formula (II) to said benzophenone is in the range of about 1:6 to about 1:9.

8. The process of claim 1, wherein step (i) is performed at a temperature in the range from about 5° C. to about 110° C.

9. The process of claim 8, which is performed at a temperature in the range from about 15° C. to about 60° C.

10. The process of claim 8, which is performed at a temperature in the range from about 20° C. to about 50° C.

11. The process of claim 1, wherein said potassium tert-alkylate is present in an amount from about 1 to about 5 equivalents relative to the amount of said alcohol of formula (II).

12. The process of claim 11, wherein said potassium tert-alkylate is present in an amount from about 1.4 to about 4 equivalents.

13. The process of claim 1, wherein said electrophilic agent of formula (IV) is used in step ii in an amount of at least one equivalent relative to the amount of potassium tert-alkylate.

14. The process of claim 1, wherein said alcohol of formula (II) is dihydrocodeine.

15. The process of claim 14, wherein said electrophilic agent of formula (IV) in step ii is selected from the group consisting of dimethyl sulfate and acetic anhydride.

16. The process of claim 5, wherein said compound of formula (IA) is selected from the group consisting of dihydrothebaine and dihydrocodeinone enol acetate.

17. A process for the preparation of a 4,5-epoxymorphinan compound of formula (I)

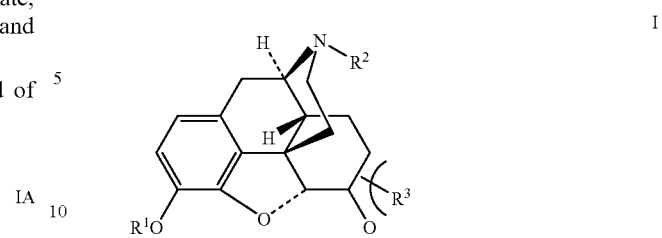

wherein
$R^1$ is methyl, substituted methyl or alcohol protecting group;
$R^2$ is hydrogen, methyl, substituted methyl or amine protecting group,
$R^3$ is methyl, substituted methyl or alcohol protecting group;
comprising the steps of
(i) reacting an alcohol of formula (II)

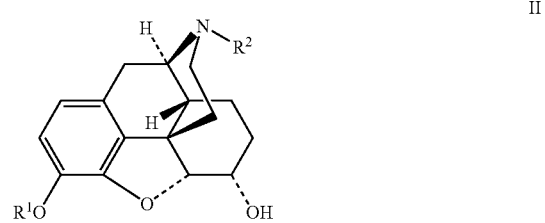

wherein $R^1$ and $R^2$ are as hereinbefore defined, with benzophenone and potassium tert-alkylate in hydrocarbon solvent to generate a reaction mixture containing the enolate of formula (III)

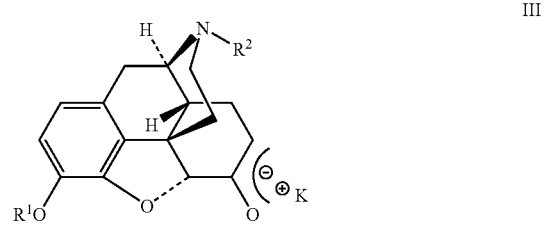

wherein $R^1$ and $R^2$ are as hereinbefore defined; and
(ii) adding the electrophilic agent of formula (IV)

$$R^3X \qquad \text{IV}$$

wherein $R^3$ is as hereinbefore defined and X is a leaving group, to the reaction mixture containing the enolate of formula (III) to yield a compound of formula (I); and
(iii) isolating the compound of formula (I).

* * * * *